United States Patent [19]

Kökösi et al.

[11] 4,404,205

[45] Sep. 13, 1983

[54] 2-OXO-2,6,7,8,9,10 HEXAHYDRO-PYRIMIDO[1,2-a]AZEPINES AND ANTIANGINAL METHOD OF USE THEREOF AND OF 4-OXO-4,6,7,8,9,10-HEXAHYDROPYRIMIDO[1,2-a]AZEPINES

[75] Inventors: József Kökösi, Budaörs; István Hermecz, Budapest; Zoltán Mészáros, Budapest; Gyorgy Szász, Budapest; Lelle Vasvári née Debreczy, Budapest; Ágnes Horváth, Budapest; Tibor Breining, Budapest, all of Hungary

[73] Assignee: Chinoin Gyogyszer es Vegyeszeti Termekek Gyara RT., Budapest, Hungary

[21] Appl. No.: 148,234

[22] Filed: May 9, 1980

[30] Foreign Application Priority Data

May 11, 1979 [HU] Hungary .............................. CI 1931

[51] Int. Cl.³ ................. C07D 487/04; A61K 31/305
[52] U.S. Cl. ..................................... 424/251; 544/282
[58] Field of Search ..................... 260/243.3; 544/282; 424/251

[56] References Cited

U.S. PATENT DOCUMENTS 3,002,000  9/1961  Tietze et al. ..................... 260/243.3
3,585,198  6/1971  Meszalos et al. .................. 424/251
3,696,197  10/1972 Meszalos et al. .................. 424/251
3,853,871  12/1974 Agata et al. ....................... 544/282

FOREIGN PATENT DOCUMENTS 318627  11/1974  Austria .
451733  11/1927  Fed. Rep. of Germany ...... 544/282
167676  6/1975   Hungary .
7212286 9/1971   Netherlands ....................... 544/282
1401820 7/1965   United Kingdom .

OTHER PUBLICATIONS

Burger Med. Chem. 2nd Ed., p. 42, Inter. (1960), N.Y. N.Y.
Burger: *Medicinal Chemistry*, 3rd Ed., Part II, pp. 1078-1082.
*The Pharmacological Basis of Therapeutics:* Goodman et al., 5th Ed. (New York 1975), pp. 326, 327, 339, 341.
Aust. J. Chem., pp. 119-127, 28 (1975).

*Primary Examiner*—Donald G. Daus
*Assistant Examiner*—D. B. Springer
*Attorney, Agent, or Firm*—Karl F. Ross; Herbert Dubno

[57] ABSTRACT

3 Substituted hexahydro-pyrimido[1, 2 a]azepines and quaternary derivatives, useful as antianginals are prepared. Specifically tested are 3 carboxylates and carbo hydrazides. 3 Cyano Carbamonyl and alkyl compounds are also disclosed.

5 Claims, No Drawings

2-OXO-2,6,7,8,9,10 HEXAHYDRO-PYRIMIDO[1,2-A]AZEPINES AND ANTIANGINAL METHOD OF USE THEREOF AND OF 4-OXO-4,6,7,8,9,10-HEXAHYDROPYRIMIDO[1,2-A]AZEPINES

The present invention relates to a process for thr preparation of 3-substituted-hexahydropyrimido[1,2-a]azepines, acid addition and quaternary salts thereof and pharmaceutical compositions containing the same and to certain 3-substituted-hexahydropyrimido[1,2-a]azepines and salts thereof which are new.

Only a few 3-substituted-pyrimido[1,2-a]azepines are disclosed in the prior art. 3-Carbamoyl-4-oxo-4,6,7,8,9,10-hexahydro-pyrimido[1,2-a]azepine is prepared in an aqueous solution of pH=10 in a 2 hour reaction from 3-carbamoyl-4-imino-4,6,7,8,9,10-hexahydro-pyrimido[1,2-a]azepine with a yield of 81%, the latter being obtained with a yield of 85% by reacting 7-ethoxy-3,4,5,6-tetrahydro-2H-azepine and amino-methylene-cyanoacetamide in a butanol solution at the boiling point of the mixture after a 48 hour reaction time and after chromatographic purification (Aust. J. Chem. 119, 28 (1975). Ethyl 4-oxo-4,6,7,8,9,10-hexahydro-pyrimido[1,2-a]azepine-3-carboxylate is obtained even by the most advantageous embodiment of the process with a yield of only 50% after complicated processing from 7-methoxy-3,4,5,6-tetrahydro-2H-azepine and diethyl ethoxymethylene-malonate in the presence of ammonium acetate (HU-Patent Spec. No. 167,676 and Japanese Pat. Spec. No. 7,334,897). 3-Cyano-4-oxo-4,6,7,8,9,10-hexahydro-azepino[1,2-a]pyrimidine is obtained in the presence of sodium ethylate from 7-amino-3,4,5,6-tetrahydro-2H-azepine and ethyl-ethoxymethylene-cyano-acetate with a yield of 16% (HU-Pat. Spec. No. 167,676 and Japanese Pat. Spec. No. 7,334,897).

We have now found that by reacting 7-amino-3,4,5,6-tetrahydro-2H-azepine of the formula III

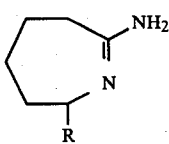

(III)

wherein
R is hydrogen or lower alkyl - containing two similar nucleophilic nitrogens
with an acrylic acid derivative of the formula IV

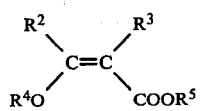

(IV)

wherein
$R^2$ is hydrogen or lower alkyl
$R^3$ is lower alkyl, phenyl, cyano, or lower alkoxycarbonyl
$R^4$ is hydrogen or lower alkyl and
$R^5$ is lower alkyl
a mixture of 4-oxo-pyrimido[1,2-a]azepine of the formula I

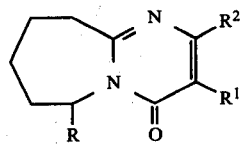

(I)

wherein
R and $R^2$ are as defined above and
$R^1$ is cyano or lower alkoxycarbonyl or lower alkyl or penyl
and of 2-oxo-pyrimido[1,2-a]azepine of the formula II

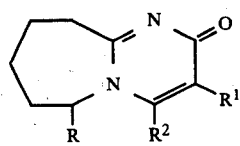

(II)

wherein
R and $R^2$ are as defined above and
$R^1$ is cyano or lower alkoxycarbonyl
is obtained, which may be if desired separated and if desired the obtained compound of the formula I or II containing alkoxycarbonyl as $R^1$ - wherein R and $R^2$ are as defined above - may be (a) saponified to a carboxylic acid of the formula I or II containing carboxyl as $R^1$ - wherein R and $R^2$ are as defined above - or may be (b) reacted with ammonia to obtain an acid amide of the formula I or II containing carbamoyl as $R^1$ - wherein R and $R^2$ are as defined above, or may be (c) reacted with hydrazine to obtain a compound of the formula I or II containing carbohydrazide as $R^1$ and R and $R^2$ are as defined above or is desired a compound of the formula I or II containing carboxyl as $R^1$ may be esterified to give a compound of the formula I or II containing alkoxycarbonyl as $R^1$ and R and $R^2$ are as defined above or a compound of the formula I or II is converted to an acid addition or quaternary salt thereof.

As starting material of the formula IV dialkyl ethoxymethylene malonate, alkyl ethoxy-methylenecyano-acetate, alkyl 2-formyl-propionate, alkyl 2-formylphenylacetate, or ethyl 2-ethyl-acetoacetate are preferably used. As alkyl esters methyl, ethyl, isopropyl, and n-propyl esters are preferred.

The term "lower alkyl" as used herein stands for straight or branched alkyl containing 1 to 4 carbon atoms, such as methyl, ethyl, isopropyl, n-propyl, isobutyl and tert. butyl.

Compounds of the formula III are preferably reacted with compounds of the formula IV in the presence of an inert solvent. As solvents preferably alcohols such as ethanol, methanol, esters such as ethyl acetate, ketones such as acetone and ethyl methyl ketone, aromatic hydrocarbons such as benzene or toluene, halogenated hydrocarbons such as chloroform, carbontetrachloride, chlorobenzene or a mixture thereof can be employed.

The reaction is preferably carried out at -15° and 150° C. According to a preferred embodiment of the process of the invention to a solution of the compound of the formula III a solution of the compound of the formula IV is added but in some cases the reverse addition may be used.

When the solvent is distilled off a mixture of the compounds of the formulae I and II is obtained. The obtained mixture may be separated according to different solubility, basicity or chromatographic behavior of the components.

The ester group in a given compound of the formula I or II - wherein R and $R^2$ are given above and $R^1$ stands for ester group - may be converted to carboxylic acid, carboxamide or carbohydrazide group by methods known per se.

When converting a compound of the formula I or II containing an ester group as $R^1$ and R and $R^2$ are as given above, to carboxylic acid, the ester group may be hydrolyzed with dilute aqueous sodium hydroxide solution, followed by acidifying with hydrochloric acid whereupon the obtained acid is precipitated and the acid is treated with aqueous or alcoholic ammonia solution or hydrazine hydrate and thus carboxamide and carbohydrazide derivatives are obtained.

By treating a given compound of the formula I or II - wherein R and $R^2$ are given above and $R^1$ represents carboxamide - with a water-removing agent such as phosphoryl chloride, a compound of the formula I or II is obtained wherein $R^1$ is cyano and R and $R^2$ are as given above. A compound of the formula I or II wherein $R^1$ stands for a carboxylic group, can be converted to a compound of the formula I or II, wherein $R^1$ represents a lower alkoxycarbonyl group, wherein R and $R^2$ are as defined above, by methods known per se. The esterification may be conducted for example by using diazoalkanes, such as diazomethane or diazoethane or an alcohol-hydrogen chloride mixture. The compounds of the formula I or II, wherein R, $R^1$ and $R^2$ are defined above, may, if desired, be reacted with acids to give salts and may be reacted with quaternizing agents to give quaternary salts. The base may be set free from the salts and if desired can be converted to other salts. Thus hydrochloric acid, hydrobromic acid, perchloric acid, acetic acid, salicylic acid salts and quaternary alkyl halides such as methyl iodide, dialkyl sulphates such as dimethy-sulphate or p-toluene-sulphonate, benzene sulphonate can be preferably prepared.

Compounds of the formula IV are commercially available products and compounds of the formula III can easily be prepared from a caprolactam containing optionally a lower alkyl group in the position 7 by reacting it with an alkylating agent such as diethyl sulphate and the obtained O-alkyl-imino-ester is converted to a compound of the formula III by reacting it with an agent setting free ammonia, such as ammonium acetate, ammonium chloride etc.

Compounds of the formula I or II, wherein R, $R^1$ and $R^2$ are as defined above, are intermediate products for the preparation of valuable pharmaceutically active compounds and also can be employed as pharmaceutically active ingredients. They are starting materials in the synthesis of compounds acting favorably on the circulating system and can be used as active ingredients of anti-anginal pharmaceutical compositions.

Compounds of the formulae I and II as active ingredients may be employed in pharmaceutical compositions containing in addition to the active ingredient inert, non-toxic solid or liquid diluents or carriers. The compositions may be administered in solid form such as tablets, capsules, dragées, or in liquid form such as solutions, suspensions or emulsions.

Compounds of the formula I and II wherein R is hydrogen or lower alkyl, $R^1$ is lower alkyl, phenyl, carboxyl, lower alkoxycarbonyl, nitrile, carbamoyl, carbohydrazido and $R^2$ is hydrogen or lower alkyl, with the provisio that if in the formula I $R^2$ is hydrogen then $R^1$ cannot stand for nitrile, alkoxycarbonyl or propyl, and pharmaceutically acceptable acid addition salts and quaternary salts thereof, are new.

The further details of the invention are illustrated by the following Examples which serve merely for illustration and not for limitation.

EXAMPLE 1

67.2 g of 7-amino-3,4,5,6-tetrahydro-2H-azepine are dissolved in 600 ml. of ethanol and the solution is cooled to $-10°$ C. and to the reaction mixture a solution of 127.8 g. of diethyl ethoxy-methylene-malonate in 600 ml. of ethanol is added dropwise under stirring within 1 hour. The reaction mixture is stirred for a further hour at a temperature of $-10°$ C. to $-5°$ C. whereafter it is boiled for 1 hour. Ethanol is distilled off at reduced pressure. The residual yellow oil containing an about 10:1 mixture of ethyl 4-oxo-4,6,7,8-hexahydro-pyrimido[1,2-a]azepine-3-carboxylate and ethyl-2-oxo-2,6,7,8,9,10-hexadhydro-pyrimido[1,2-a]azepine-3-carboxylate is dissolved in 600 ml. of benzene and shaken out twice subsequently with 60 ml of water. The benzene soltuion is dried over anhydrous sodium sulphate and evaporated at reduced pressure. 114 g. (80.5%) ethyl 4-oxo-4,6,7,8,9,10-hexahydro-pyrimido[1,2-a]azepine-3-carboxylate are obtained melting at 82°–84° C. after recrystallization from ethyl acetate.

Analysis for the formula $C_{12}H_{16}N_2O_3$: calculated: C 61.00%; H 6.82%; N 11.85% found: C 60.82%; H 6.91%; N 11.79%.

The combined aqueous solution is shaken out twice subsequently with 120 ml. of chloroform and the combined chloroform solution, dried over calcinated sodium sulphate, is evaporated at reduced pressure. Thus 2.1 g. (8.9%) of ethyl 2-oxo-2,6,7,8,9,10-hexahydro-pyrimido[1,2-a]azepine-3-carboxylate are obtained melting at 156°–157° C.

Analysis for the formula $C_{12}H_{16}N_2O_3$: calculated: C 61.00%; H 6.82%; N 11.85% found: C 60.91%; H 6.87%; N 11.81%.

EXAMPLE 2

11.2 g. of 2-amino-3,4,5,6-tetrahydro-2H-azepine are dissolved in 70 ml. of ethanol and to the solution under stirring at 0° C. a solution of 16.9 g. of ethyl ethoxy-methylene-cyanoacetate in 120 ml. of ethanol is added dropwise within 1 hour. The reaction mixture is then stirred for 1 hour at room temperature and 1 hour under boiling. Ethanol is distilled off at reduced pressure. The residual red oil containing an about 3:1 mixture of 3-cyano-4-oxo-4,6,7,8,9,10-hexahydro-pyrimido[1,2-a]azepine and 3-cyano-2-oxo-2,6,7,8,9,10-hexahydro-pyrimido[1,2-a]azepine is dissolved in 200 ml of benzene and shaken out twice subsequently with 5% by W/V hydrochloric acid solution and then with water.

The benzene solution dried over anhydrous sodium sulphate is evaporated at reduced pressure and the residue is crystallized from ethanol. Thus 4.6 g. (24.2%) 3-cyano-4-oxo-4,6,7,8,9,10-hexahydro-pyrimido[1,2-a]azepine are obtained melting at 125° C.

Analysis for the formula $C_{10}H_{11}N_3O$: calculated: C 63.51%; H 5.86%; N 22.22% found: C 63.95%; H 5.89%; N 22.08%.

The combined aqueous layers are neutralized with solid sodium hydrogen carbonate and shaken out with chloroform. The combined chloroform solution dried above sodium sulphate is evaporated at reduced pressure and the residue is crystallized from ethanol. 1.7 g. (8.9%) 3-cyano-2-oxo-2,6,7,8,9,10-hexahydropyrimido[1,2-a]azepine is obtained melting at 205°–206° C.

Analysis for the formula $C_{10}H_{11}N_3O$: calculated: C 63.51%; H 5.86%; N 22.22%; found: C 63.92%; H 5.90%; N 21.97%.

EXAMPLE 3

To a solution of 11.2 g. of 7-amino-3,4,5,6-tetrahydro-2H-azepine in 100 ml. ethanol 13.1 g. of ethyl 2-formylpropionate are added at room temperature and the reaction mixture is stirred for 24 hours and boiled for 3 hours. Ethanol is then evaporated at reduced pressure and the residue is treated with a mixture of acetone and petroleum ether. The precipitated crystals are filtered. 6.6 g. (37%) of 3-methyl-2-oxo-2,6,7,8,9,10-hexahydropyrimido[1,2-a]azepine are obtained, melting at 202° C. after boiling in acetone.

Analysis for the formula $C_{10}H_{14}N_2O$: calculated: C 67.39%; H 7.91%; N 15.71% found: C 67.18%; H 8.00%; N 15.72%.

The mother liquor containing acetone and petrolether is evaporated. The obtained orange-red oil is dissolved in 50 ml. of benzene, treated with declorizing charcoal and saturated with dry hydrochloric acid gas. The obtained crystals are filtered. 5.75 g. (26.7%) of 3-methyl-4-oxo-4,6,7,8,9,10-hexahydro-pyrimido[1,2-a]azepine-hydrochloride are obtained melting at 207° C.

Analysis for the formula $C_{10}H_{15}N_2OCl$: calculated: C 55.94%; H 7.04%; N 13.04%; Cl 16.51%; found: C 56.05%; H 7.01%; N 12.98%; Cl 16.70%.

EXAMPLE 4

11.8 g. of ethyl 4-oxo-4,6,7,8,9,10-hexahydropyrimido[1,2-a]azepine-3-carboxylate are dissolved in 40 ml. of 30% by wieght ammonium hydroxide solution and the reaction mixture is allowed to stand at room temperature for 2 hours. The precipitated crystals are filtered and washed with water. 10.1 g. (97.5%) of 3-carbamoyl-4-oxo-4,6,7,8,9,10-hexahydro-pyrimido[1,2-a]azepine are obtained melting at 234°–235° C.

Analysis for the formula $C_{10}H_{13}N_3O_2$: calculated: C 57.96%; H 6.32%; N 20.27%; found: C 57.88%; H 6.30%; N 20.34%.

EXAMPLE 5

One may proceed as described in Example 4 but as starting material ethyl 2-oxo-2,6,7,8,9,10-hexahydropyrimido[1,2-a]azepine-3-carboxylate is used and 3-carbamoyl-2-oxo-2,6,7,8,9,10-hexahydro-pyrimido-[1,2-a]azepine are obtained melting at 219° C. Yield: 69%.

Analysis for the formula $C_{10}H_{13}N_3O_2$: calculated: C 57.96%; H 6.32%; N 20.27%; found: C 58.07%; H 6.30%; N 20.30%.

EXAMPLE 6

11.8 g. of ethyl 4-oxo-4,6,7,8,9,10,-hexahydropyrimido[1,2-a]azepine are dissolved in 50 ml. of 5% by W/V sodium hydroxide solution and the solution is allowed to stand at room temperature for 2 hours. The pH value of the solution is adjusted to three by adding 36% by W/V hydrochloric acid solution. The precipitated crystals are filtered and washed with water. 9.25 g. (91%) of 4-oxo-4,6,7,8,9,10-hexahydro-pyrimido[1,2-a]azepine-3-carboxylic acid are obtained melting at 117°–119° C. after recrystallization from methanol (decomposition).

Analysis for the formula $C_{10}H_{12}N_2O_3$: calculated: C 57.69%; H 5.81%; N 13.45%; found: C 57.27%; H 5.84%; N 13.23%.

EXAMPLE 7

One may proceed as disclosed in Example 6 but as starting material ethyl 2-oxo-2,6,7,8,9,10-hexahydropyrimido[1,2-a]azepine-3-carboxylate is used and 2-oxo-2,6,7,8,9,10-hexahydro-pyrimido[1,2-a]azepine-3carboxylic acid is obtained with a yield of 67.4% melting at 198° C. under decomposition.

Analysis for the formula $C_{10}H_{12}N_2O_3$: calculated: C 57.69%; H 5.81%; N 13.45%; found: C 57.31%; H 5.88%; N 13.21%.

EXAMPLE 8

A solution of 2.36 g. of ethyl 4-oxo-4,6,7,8,9,10-hexahydro-pyrimido[1,2-a]azepine-3-carboxylate in 10 ml. of 98% by W/V hydrazine hydrate is allowed to stand at room temperature for 2 hours. The precipitated crystals are filtered and washed with water and ethanol. 1.8 g. of (81%) 4-oxo-4,6,7,8,9,10-hexahydro-pyrimido[1,2-a]azepine-3-carbohydrazide are obtained melting at 184°–186° C.

Analysis for the formula $C_{10}H_{14}N_2O_2$: calculated: C 54.04%; H 6.35%; N 25.21%; found: C 53.93%; H 6.41%; N 25.48%.

EXAMPLE 9

One may proceed according to Example 8 but as starting material ethyl 2-oxo-2,6,7,8,9,10-hexahydropyrimido[1,2-a]azepine-3-carboxylate is used and 2-oxo-2,6,7,8,9,10-hexahydro-pyrimido[1,2-azepine-3-carbohydrazide is obtained with a yield 74.3% melting at 201° C.

Analysis for the formula $C_{10}H_{14}N_4O_2$: calculated: C 54.04%; H 6.32%; N 25.21%; found: C 53.84%; H 6.42%; N 25.36%.

EXAMPLE 10

1.18 g. of ethyl 4-oxo-4,6,7,8,9,10-hexahydropyrimido[1,2-a]azepine-3-carboxylate is dissolved in 12 ml. of acetone and allowed to stand for 24 hours at room temperature in the presence of 1.25 ml. of methyl iodide. The reaction mixture is diluted with diethyl ether. The precipitated crystals are filtered. 0.8 g. (43%) of 3-ethoxycarbonyl-1-methyl-4-oxo-4,6,7,8,9,10-hexahydro-pyrimido[1,2-a]azepinium iodide is obtained melting at 202°–204° C.

Analysis for the formula $C_{13}H_{19}N_2O_3I$: calculated: C 41.28%; H 5.06%; N 7.40%; I 33.55%; found: C 41.46%; H 5.18%; N 7.30%; I 33.55%.

EXAMPLE 11

2.36 g. of ethyl 2-oxo-2,6,7,8,9,10-hexahydropyrimido[1,2-a]azepine-3-carboxylate are dissolved in 5 ml. of ethanol in the presence of 5 ml. methyl iodide and the solution is allowed to stand for 72 hours at room temperature. The alcohol is removed by evaporation. The residual oil is treated with 20 ml. of ethyl acetate. Ethyl acetate is decanted. The obtained hygroscopic oil is dried.

Analysis for the formula $C_{13}H_{19}N_2O_3I$: calculated: C 41.28%; H 5.06%; N 7.40%; I 33.55%; found: C 41.52%; H 5.12%; N 7.14%; I 32.97%.

EXAMPLE 12

4.14 g. of 3-carbamoyl-4-oxo-4,6,7,8,9,10-hexahydro-pyrimido[1,2-a]azepine are boiled in 50 ml. methanol with 1.3 ml. of dimethyl sulphate for 1 hour whereafter the reaction mixture is concentrated to half volume and allowed to crystallize upon cooling below 0° C. The precipitated crystals are filtered. 5.5 g. of 3-carbamoyl-1-methyl-4-oxo-4,6,7,8,9,10-hexahydro-pyrimido[1,2-a]azepinium-methyl sulphate are obtained melting at 191°–193° C.

Analysis for the formula $C_{12}H_{19}N_3O_6S$: calculated: C 43.23%; H 5.74%; N 12.60%; S 9.62%; found: C 43.05%; H 5.61%; N 12.58%; S 9.53%.

EXAMPLE 13

11.2 g. of 7-amino-3,4,5,6-tetrahydro-2H-azepine and 19.2 g. of ethyl 2-formyl-phenylacetate are boiled in 100 ml. abs. alcohol for 5 hours whereafter the reaction mixture is evaporated. The residue is treated with a mixture of acetone and petroleum ether. The obtained solid is filtered. 22 g. (91%) of a mixture of 3-phenyl-2-oxo-2,6,7,8,9,10-hexahydro-pyrimido[1,2-a]azepine and 3phenyl-4-4,6,7,8,9,10-hexahydro-pyrimido[1,2-a]azepine is obtained melting in the range of from 126° to 130° C.

Analysis for the formula $C_{15}H_{16}N_2O$: calculated: C 74.97%; H 6.71%; N 11.66%; found: C 74.21%; H 6.58%; N 11.44%.

EXAMPLE 14

1 g. of a mixture of 3-phenyl-2-oxo-2,6,7,8,9,10-hexahydro-pyrimido[1,2-a]azepine and 3-phenyl-4-oxo-4,6,7,8,9,10-hexahydro-pyrimido[1,2-a]azepine obtained according to Example 13 is applied to a silica gel column of a diameter of 1 cm. consisting of 10 g. silica gel of particle size 0.063–0.125 mm. and eluted with ethyl acetate. After evaporating the ethyl acetate eluate pure 3-phenyl-4-oxo-4,6,7,8,9,10-hexahydro-pyrimido[1,2-a]azepine is obtained melting at 156°–158° C.

Analysis for the formula $C_{15}H_{16}N_2O$: calculated: C 74.97%; H 6.71%; N 11.66%; found: C 74.93%; H 6.70%; N 11.58%.

The elution of the column is continued after removing 3-phenyl-4-oxo-4,6,7,8,9,10-hexahydro-pyrimido[1,2-a]azepine with methanol and after evaporating the methanol eluate 3-phenyl-2-oxo-2,6,7,8,9,10-hexahydro-pyrimido[1,2-a]azepine is obtained melting at 215°–216° C.

Analysis for the formula $C_{15}H_{16}N_2O$: calculated: C 74.97%; H 6.71%; N 11.66%; found: C 74.85%; H 6.68%; N 11.42%.

EXAMPLE 15

5.6 g. of 7-amino-3,4,5,6-tetrahydro-2H-azepine and 7.5 g. of ethyl 2-ethyl-acetoacetate are boiled in 50 ml. ethanol for 3 hours. The ethanol is then evaporated at reduced pressure. The residual oil is dissolved in 20 ml. of 10% hydrochloric acid and shaken out twice with 10 ml. ethyl acetate. The aqueous layer is neutralized with sodium hydrogen carbonate and shaken out with 3×10 ml. chloroform. The combined chloroform layer is dried over calcinated sodium sulphate and evaporated. The residual colorless oil is fractionated at reduced pressure. 6.3 g. (61%) 3-ethyl-2-methyl-4-oxo-4,6,7,8,9,10-hexahydropyrimido[1,2-a]azepine are obtained. Boiling point: 156°–160° C./2 mmHg.

Analysis for the formula $C_{12}H_{18}N_2O$: calculated: C 69.87%; H 8.79%; N 13.58%; found: C 69.98%; H 8.85%; N 13.22%.

EXAMPLE 16

12.6 g. 2-amino-7-methyl-3,4,5,6-tetrahydro-2H-azepine are dissolved in 100 ml. ethanol and the solution is added dropwise at −5°–0° C. to a solution of 22.6 g. diethylethoxy-methylene-malonate in 100 ml. ethanol. When the solution is added the reaction mixture is allowed to warm up to room temperature and allowed to stand for 24 hours. The solvent is then removed by evaporation.

The residual oil is then dissolved in 100 ml. of 10% by W/V hydrochloric acid and shaken out twice with 10 ml. diethyl ether. The aqueous layer is neutralized with sodium hydrogen carbonate and shaken out four-times with 15 ml. of ethyl acetate. The ethyl acetate layers are evaporated after drying above sodium sulphate and after filtration. The residual oil is taken up in acetone and treated with dry hydrochloric acid gas whereupon white crystals are precipitated. 15.5 g. of ethyl-6-methyl-4-oxo-4,6,7,8,9,10-hexahydro-pyrimido[1,2-a]azepine-3-carboxylate-hydrochloride are obtained.

Yield: 56%.

Melting point: 168°–172° C.

Analysis for the formula $C_{13}H_{19}N_2O_3Cl$: calculated: C 54.64%; H 6.70%; N 9.80%; found: C 54.31%; H 6.72%; N 9.76%.

EXAMPLE 17

2.52 g. of 2-amino-7-methyl-3,4,5,6-tetrahydro-2H-azepine are dissolved in 25 ml. of ethanol and the solution is added dropwise to a solution of 3.38 g. of ethoxymethylene-cyanoacetate in 25 ml. ethanol at −5° C. The reaction mixture is stirred for 1 hour at −5° C. and allowed to warm up to room temperature and boiled for 1 hour. The solvent is evaporated. The residual oil is dissolved in 40 ml. of benzene and the solution is shaken out once with 10 ml. of 5% by W/V sodium carbonate solution and twice with 10 ml. of water. The benzene layer is dried above sodium sulphate and evaporated after filtration. The residual oil is crystallized from acetone. 1.26 g. (31%) 3-cyano-6-methyl-4-oxo-4,6,7,8,9,10-hexahydro-pyrimido[1,2-a]azepine is obtained melting at 154° C.

Analysis for the formula $C_{11}H_{13}N_3O$: calculated: C 65.00%; H 6.42%; N 20.67%; found: C 64.32%; H 6.48%; N 20.77%.

Pharmacological test results

The antianginal activity of the compounds was determined in rats by inhibiting acute coronary insufficiency induced by intravenously administered vasopressin (Arch. Int. Pharmacodyn. 1966, 160, 147). Test-compounds were administered in an aqueous solution intravenously.

| Compound | i.v. dosage | protective activity % (rat) |
| --- | --- | --- |
| 4-oxo-4,6,7,8,9,10-hexahydro-pyrimido[1,2-a]-azepine-3-carbohydrazide | 10 mg./kg. | 50.1% |
| Ethyl-4-oxo-4,6,7,8,9,10-hexahydro-pyrimido[1,2-a]-azepine-3-carboxylate | 10 mg./kg. | 77.6% |
| Ethyl-2-oxo-2,6,7,8,9,10- | 10 mg./kg. | 85.2% |

| Compound | i.v. dosage | protective activity % (rat) |
|---|---|---|
| hexahydro-pyrimido[1,2-a]-azepine-3-carboxylate | | |
| Papaverine | 2 mg./kg. | 36.9% |

We claim:

1. A compound of the formula II

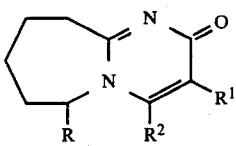

(II)

or a pharmaceutically acceptable acid addition or quaternary ammonium salt thereof wherein the quaternizing group is a lower alkyl, phenyl or lower alkyl phenyl group and wherein R is hydrogen or lower alkyl, R$^1$ is C$_1$ to C$_4$ alkyl, phenyl, carboxyl, C$_1$ to C$_4$ alkoxycarbonyl, nitrile, carbamoyl or carbohydrazido; and R$^2$ is hydrogen or C$_1$ to C$_4$ alkyl.

2. The compound defined in claim 1 which is ethyl-2-oxo-2,6,7,8,9,10-hexahydro-pyrimido(1,2-a)azepine-3-carboxylate or a pharmaceutically acceptable acid addition or quaternary ammonium salt thereof, wherein the quaternizing group is a lower alkyl, phenyl or lower alkyl phenyl group.

3. An antianginal pharmaceutical composition which comprises as an active ingredient a pharmaceutically effective amount of the compound defined in claim 1 or a pharmaceutically acceptable acid addition or quaternary ammonium salt thereof wherein the quaternizing group is a lower alkyl, phenyl, or lower alkyl phenyl group and an inert pharmaceutically acceptable carrier.

4. An anti-anginal method of treatment which comprises the step of administering to an animal suffering from angina a pharmaceutically effective amount of a compound of the formula (I)

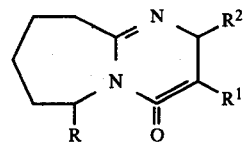

or formula (II)

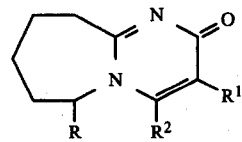

or a mixture thereof or a pharmaceutically acceptable acid addition or quaternary ammonium salt thereof wherein the quaternary group is a lower alkyl, phenyl or lower alkyl phenyl group; and
wherein R$^1$ is C$_1$ to C$_4$ alkyl, phenyl, carboxyl, C$_1$ to C$_4$ alkoxycarbonyl, nitrile, carbamoyl, or carbohydrazido; and R$^2$ is hydrogen or C$_1$ to C$_4$ alkyl.

5. An anti-anginal method of treatment which comprises the step of administering to an animal suffering from angina a pharmaceutically effective amount of a compound selected from the group which consists of:
ethyl-2-oxo-2,6,7,8,9,10-hexahydro-pyrimido[1,2-a]azepine-3-carboxylate;
4-oxo-4,6,7,8,9,10-hexahydro-pyrimido[1,2-a]azepine-3-carbohydrazide; and
ethyl-4-oxo-4,6,7,8,9,10-hexahydro-pyrimido[1,2-a]azepine-3-carboxylate.

* * * * *